(12) United States Patent
Vortman et al.

(10) Patent No.: US 8,088,067 B2
(45) Date of Patent: *Jan. 3, 2012

(54) TISSUE ABERRATION CORRECTIONS IN ULTRASOUND THERAPY

(75) Inventors: Kobi Vortman, Haifa (IL); Shuki Vitek, Haifa (IL)

(73) Assignee: Insightec Ltd., Tirat Carmel (IL)

( * ) Notice: Subject to any disclaimer, the term of this patent is extended or adjusted under 35 U.S.C. 154(b) by 2268 days.

This patent is subject to a terminal disclaimer.

(21) Appl. No.: 10/328,584

(22) Filed: Dec. 23, 2002

(65) Prior Publication Data

US 2004/0122323 A1 Jun. 24, 2004

(51) Int. Cl.
*A61B 8/08* (2006.01)
(52) U.S. Cl. ......... 600/437; 600/411; 600/425; 382/128
(58) Field of Classification Search .................. 600/439, 600/427; 601/2–4
See application file for complete search history.

(56) References Cited

U.S. PATENT DOCUMENTS

| | | | |
|---|---|---|---|
| 2,795,709 A | 6/1957 | Camp | |
| 3,142,035 A | 7/1964 | Harris | |
| 3,942,150 A | 3/1976 | Booth et al. | |
| 3,974,475 A | 8/1976 | Burckhardt et al. | |
| 3,992,693 A | 11/1976 | Martin et al. | |
| 4,000,493 A | 12/1976 | Spaulding et al. | |
| 4,339,952 A | 7/1982 | Foster | |
| 4,454,597 A | 6/1984 | Sullivan | |
| 4,478,083 A | 10/1984 | Hassler et al. | |
| 4,505,156 A | 3/1985 | Questo | |
| 4,526,168 A | 7/1985 | Hassler et al. | |
| 4,537,074 A | 8/1985 | Dietz | |
| 4,549,533 A | 10/1985 | Cain et al. | |
| 4,858,597 A | 8/1989 | Kurtze et al. | |
| 4,865,042 A | 9/1989 | Umemura et al. | |
| 4,888,746 A | 12/1989 | Wurster et al. | |
| 4,889,122 A | 12/1989 | Watmough et al. | |
| 4,893,284 A | 1/1990 | Magrane | |

(Continued)

FOREIGN PATENT DOCUMENTS

DE 4345308 C2 2/2001

(Continued)

OTHER PUBLICATIONS

Huber et al. A New Noninvasive Approach in Breast Cancer Therapy Using Magnetic Resonance Imaging-guided Focused Ultrasound Surgery. Cancer Research 61, 8441-8447, Dec. 1, 2001].*

(Continued)

*Primary Examiner* — Parikha Mehta
(74) *Attorney, Agent, or Firm* — Bingham McCutchen LLP (57) ABSTRACT

A system for focusing ultrasonic energy through intervening tissue into a target site within a tissue region includes a transducer array including transducer element, an imager for imaging the tissue region, a processor receiving images from the imager to determine boundaries between different tissue types within the intervening tissue and generate correction factors for the transducer elements to compensate for refraction occurring at the boundaries between the tissue types and/or for variations in speed of sound. A controller is coupled to the processor and the transducer array to receive the correction factors and provide excitation signals to the transducer elements based upon the correction factors. The correction factors may include phase and/or amplitude correction factors, and the phases and/or amplitudes of excitation signals provided to the transducer elements may be adjusted based upon the phase correction factors to focus the ultrasonic energy to treat tissue at the target site.

26 Claims, 4 Drawing Sheets

U.S. PATENT DOCUMENTS

| | | | |
|---|---|---|---|
| 4,937,767 A | 6/1990 | Reuschel et al. |
| 5,209,221 A | 5/1993 | Riedlinger |
| 5,247,935 A | 9/1993 | Cline et al. |
| 5,271,400 A | 12/1993 | Dumoulin et al. |
| 5,275,165 A | 1/1994 | Ettinger et al. |
| 5,291,890 A | 3/1994 | Cline et al. |
| 5,307,812 A | 5/1994 | Hardy et al. |
| 5,307,816 A | 5/1994 | Hashimoto et al. |
| 5,318,025 A | 6/1994 | Dumoulin et al. |
| 5,323,779 A | 6/1994 | Hardy et al. |
| 5,327,884 A | 7/1994 | Hardy et al. |
| 5,329,930 A | 7/1994 | Thomas, III et al. |
| 5,368,031 A | 11/1994 | Cline et al. |
| 5,368,032 A | 11/1994 | Cline et al. |
| 5,379,642 A | 1/1995 | Reckwerdt et al. |
| 5,391,140 A | 2/1995 | Schaetzle et al. |
| 5,413,550 A | 5/1995 | Castel |
| 5,443,068 A | 8/1995 | Cline et al. |
| 5,474,071 A | 12/1995 | Chapelon et al. |
| 5,485,839 A | 1/1996 | Aida et al. |
| 5,490,840 A | 2/1996 | Uzgiris et al. |
| 5,507,790 A | 4/1996 | Weiss |
| 5,520,188 A | 5/1996 | Hennige et al. |
| 5,526,814 A | 6/1996 | Cline et al. |
| 5,549,638 A | 8/1996 | Burdette |
| 5,553,618 A | 9/1996 | Suzuki et al. |
| 5,573,497 A | 11/1996 | Chapelon |
| 5,582,578 A | 12/1996 | Zhong et al. |
| 5,590,653 A | 1/1997 | Aida et al. |
| 5,601,526 A | 2/1997 | Chapelon et al. |
| 5,605,154 A | 2/1997 | Ries et al. |
| 5,617,371 A | 4/1997 | Williams |
| 5,617,857 A | 4/1997 | Chader et al. |
| 5,643,179 A | 7/1997 | Fujimoto |
| 5,662,170 A | 9/1997 | Donovan et al. |
| 5,665,054 A | 9/1997 | Dory |
| 5,666,954 A | 9/1997 | Chapelon et al. |
| 5,676,673 A | 10/1997 | Ferre et al. |
| 5,687,729 A | 11/1997 | Schaetzle |
| 5,694,936 A | 12/1997 | Fujimoto et al. |
| 5,711,300 A | 1/1998 | Schneider et al. |
| 5,722,411 A | 3/1998 | Suzuki et al. |
| 5,739,625 A | 4/1998 | Falcus |
| 5,743,863 A | 4/1998 | Chapelon |
| 5,759,162 A | 6/1998 | Oppelt et al. |
| 5,769,790 A | 6/1998 | Watkins et al. |
| 5,810,008 A | 9/1998 | Dekel et al. |
| 5,873,845 A | 2/1999 | Cline et al. |
| 5,897,495 A | 4/1999 | Aida et al. |
| 5,938,600 A | 8/1999 | Van Vaals et al. |
| 5,938,608 A | 8/1999 | Bieger et al. |
| 5,947,900 A | 9/1999 | Derbyshire et al. |
| 5,984,881 A | 11/1999 | Ishibashi et al. |
| 6,004,269 A | 12/1999 | Crowley et al. |
| 6,023,636 A | 2/2000 | Wendt et al. |
| 6,042,556 A * | 3/2000 | Beach et al. ............ 601/3 |
| 6,071,239 A | 6/2000 | Cribbs et al. |
| 6,113,559 A | 9/2000 | Klopotek |
| 6,128,522 A | 10/2000 | Acker et al. |
| 6,128,958 A | 10/2000 | Cain |
| 6,193,659 B1 | 2/2001 | Ramamurthy et al. |
| 6,242,915 B1 | 6/2001 | Hurd |
| 6,263,230 B1 | 7/2001 | Haynor et al. |
| 6,267,734 B1 | 7/2001 | Ishibashi et al. |
| 6,289,233 B1 | 9/2001 | Dumoulin et al. |
| 6,309,355 B1 | 10/2001 | Cain et al. |
| 6,334,846 B1 | 1/2002 | Ishibashi et al. |
| 6,374,132 B1 | 4/2002 | Acker et al. |
| 6,392,330 B1 | 5/2002 | Zloter et al. |
| 6,397,094 B1 | 5/2002 | Ludeke et al. |
| 6,413,216 B1 | 7/2002 | Cain et al. |
| 6,419,648 B1 | 7/2002 | Vitek et al. |
| 6,424,597 B1 | 7/2002 | Bolomey et al. |
| 6,428,532 B1 | 8/2002 | Doukas et al. |
| 6,461,314 B1 | 10/2002 | Pant et al. |
| 6,475,150 B2 | 11/2002 | Haddad |
| 6,478,739 B1 | 11/2002 | Hong |
| 6,506,154 B1 | 1/2003 | Ezion et al. |
| 6,506,171 B1 | 1/2003 | Vitek et al. |
| 6,511,428 B1 | 1/2003 | Azuma et al. |
| 6,522,142 B1 | 2/2003 | Freundlich |
| 6,523,272 B1 | 2/2003 | Morales |
| 6,559,644 B2 | 5/2003 | Froundlich et al. |
| 6,566,878 B1 | 5/2003 | Komura et al. |
| 6,582,381 B1 | 6/2003 | Yehezkeli et al. |
| 6,599,256 B1 | 7/2003 | Acker et al. |
| 6,612,988 B2 | 9/2003 | Maor et al. |
| 6,613,004 B1 | 9/2003 | Vitek et al. |
| 6,613,005 B1 | 9/2003 | Friedman et al. |
| 6,618,608 B1 | 9/2003 | Watkins et al. |
| 6,618,620 B1 | 9/2003 | Freundlich et al. |
| 6,626,854 B2 | 9/2003 | Friedman et al. |
| 6,626,855 B1 | 9/2003 | Weng et al. |
| 6,629,929 B1 | 10/2003 | Jago et al. |
| 6,645,162 B2 | 11/2003 | Friedman et al. |
| 6,666,833 B1 | 12/2003 | Friedman et al. |
| 6,676,601 B1 | 1/2004 | Lacoste et al. |
| 6,679,855 B2 | 1/2004 | Horn et al. |
| 6,705,994 B2 * | 3/2004 | Vortman et al. ............ 600/443 |
| 6,719,694 B2 | 4/2004 | Weng et al. |
| 6,733,450 B1 | 5/2004 | Alexandrov et al. |
| 6,735,461 B2 | 5/2004 | Vitek et al. |
| 6,761,691 B2 | 7/2004 | Tsuzuki |
| 6,770,031 B2 | 8/2004 | Hynynen et al. |
| 6,770,039 B2 | 8/2004 | Zhong et al. |
| 6,788,619 B2 | 9/2004 | Calvert |
| 6,790,180 B2 | 9/2004 | Vitek |
| 6,824,516 B2 | 11/2004 | Batten et al. |
| 6,951,540 B2 | 10/2005 | Ebbini et al. |
| 6,961,606 B2 | 11/2005 | DeSilets et al. |
| 7,001,379 B2 | 2/2006 | Behl et al. |
| 7,077,820 B1 | 7/2006 | Kadziauskas et al. |
| 7,094,205 B2 | 8/2006 | Marmarelis |
| 7,128,711 B2 | 10/2006 | Medan et al. |
| 7,175,596 B2 | 2/2007 | Vitek et al. |
| 7,175,599 B2 | 2/2007 | Hynynen et al. |
| 7,264,592 B2 | 9/2007 | Shehada |
| 7,264,597 B2 | 9/2007 | Cathignol |
| 7,267,650 B2 | 9/2007 | Chow et al. |
| 7,344,509 B2 | 3/2008 | Hynynen et al. |
| 7,377,900 B2 | 5/2008 | Vitek et al. |
| 7,505,808 B2 | 3/2009 | Anderson et al. |
| 7,510,536 B2 | 3/2009 | Foley et al. |
| 7,511,501 B2 | 3/2009 | Wexler |
| 7,535,794 B2 | 5/2009 | Prus et al. |
| 7,553,284 B2 | 6/2009 | Vaitekunas |
| 7,603,162 B2 | 10/2009 | Danz et al. |
| 7,611,462 B2 | 11/2009 | Vortman et al. |
| 7,652,410 B2 | 1/2010 | Prus |
| 7,699,780 B2 | 4/2010 | Vitek et al. |
| 2001/0031922 A1 | 10/2001 | Weng et al. |
| 2002/0035779 A1 | 3/2002 | Krieg et al. |
| 2002/0082589 A1 | 6/2002 | Friedman et al. |
| 2003/0004439 A1 | 1/2003 | Pant et al. |
| 2003/0060820 A1 | 3/2003 | Maguire et al. |
| 2003/0187371 A1 | 10/2003 | Vortman et al. |
| 2004/0030251 A1 | 2/2004 | Ebbini et al. |
| 2004/0068186 A1 | 4/2004 | Ishida et al. |
| 2004/0122323 A1 | 6/2004 | Vortman et al. |
| 2004/0210134 A1 | 10/2004 | Hynynen et al. |
| 2005/0033201 A1 | 2/2005 | Takahashi et al. |
| 2005/0096542 A1 | 5/2005 | Weng et al. |
| 2005/0203444 A1 | 9/2005 | Schonenberger et al. |
| 2005/0251046 A1 | 11/2005 | Yamamoto et al. |
| 2006/0052661 A1 | 3/2006 | Gannot et al. |
| 2006/0052701 A1 | 3/2006 | Carter et al. |
| 2006/0058671 A1 * | 3/2006 | Vitek et al. ............ 600/447 |
| 2006/0058678 A1 | 3/2006 | Vitek et al. |
| 2006/0106300 A1 | 5/2006 | Seppenwoolde et al. |
| 2006/0173385 A1 | 8/2006 | Lidgren et al. |
| 2006/0206105 A1 | 9/2006 | Chopra et al. |
| 2006/0229594 A1 | 10/2006 | Francischelli et al. |
| 2007/0016039 A1 | 1/2007 | Vortman et al. |
| 2007/0055140 A1 | 3/2007 | Kuroda |
| 2007/0098232 A1 | 5/2007 | Matula et al. |
| 2007/0167781 A1 | 7/2007 | Vortman et al. |
| 2007/0197918 A1 | 8/2007 | Vitek et al. |

| | | | |
|---|---|---|---|
| 2008/0027342 | A1 | 1/2008 | Rouw et al. |
| 2008/0031090 | A1 | 2/2008 | Prus et al. |
| 2008/0033278 | A1 | 2/2008 | Assif |
| 2008/0082026 | A1 | 4/2008 | Schmidt et al. |
| 2008/0108900 | A1 | 5/2008 | Lee et al. |
| 2008/0183077 | A1 | 7/2008 | Moreau-Gobard et al. |
| 2009/0088623 | A1 | 4/2009 | Vortman et al. |
| 2010/0056962 | A1 | 3/2010 | Vortman et al. |

FOREIGN PATENT DOCUMENTS

| | | |
|---|---|---|
| EP | 1774920 A1 | 4/2007 |
| FR | 2806611 A1 | 9/2001 |
| JP | 11313833 A | 11/1999 |
| WO | WO-9100059 A1 | 1/1991 |
| WO | WO-9852465 A1 | 11/1998 |
| WO | WO-0031614 A1 | 6/2000 |
| WO | WO-0166189 A1 | 9/2001 |
| WO | WO-0180709 A2 | 11/2001 |
| WO | WO 02/058791 A1 | 8/2002 |
| WO | WO-03/013654 | 2/2003 |
| WO | WO-03097162 A2 | 11/2003 |
| WO | WO-03098232 A2 | 11/2003 |
| WO | WO-2005058029 A2 | 6/2005 |
| WO | WO-2006018837 A2 | 2/2006 |
| WO | WO-2006025001 A1 | 3/2006 |
| WO | WO-2006087649 A1 | 8/2006 |
| WO | WO-2007073551 A1 | 6/2007 |
| WO | WO-2008050278 A1 | 5/2008 |
| WO | WO-2008075203 A2 | 6/2008 |
| WO | WO-2008119054 A1 | 10/2008 |
| WO | WO-2009055587 A1 | 4/2009 |

OTHER PUBLICATIONS

Vykhodtseva et al. MRI Detection of the Thermal Effects of Focused Ultrasound on the Brain. Ultrasound in Med. & Biol., vol. 26, No. 5, pp. 871-880, 2000.*
Jolesz et al. Integration of Interventional MRI With Computer-Assisted Surgery. Journal of Magnetic Resonance Imaging 13:69-77 (2001).*
Botros et al. A Hybrid Computational Model for Ultrasound Phased-Array Heating in Presence of Strongly Scattering Obstacles. IEEE Transactions on Biomedical Engineering, vol. 44, No. 11, Nov. 1997.*
Botros et al., "A hybrid computational model for ultrasound phased-array heating in presence of strongly scattering obstacles," IEEE Trans. on Biomed. Eng., vol. 44, No. 11, pp. 1039-1050 (Nov. 1997).
Cain et al., "Concentric-ring and Sector-vortex Phased-array Applicators for Ultrasound Hperthermia," IEEE Trans. on Microwave Theory & Techniques, vol. MTT-34, No. 5, pp. 542-551 (May 1986).
Chen et al., "MR Acoustic Radiation Force Imaging: Comparison of Encoding Gradients."
Cline et al., "Focused US system for MR imaging-guide tumor ablation," Radiology, v. 194, No. 3, pp. 731-738 (Mar. 1995).
Cline et al., "MR Temperature mapping of focused ultrasound surgery," Magnetic Resonance in Medicine, vol. 32, No. 6, pp. 628-636 (1994).
Cline et al., "Simultaneous magnetic resonance phase and magnitude temperature maps in muscle," Magnetic Resonance in Medicine, vol. 35, No. 3, pp. 309-315 (Mar. 1996).
Daum et al., "Design and evaluation of a feedback based phased array system for ultrasound surgery," IEEE Trans. Ultrason. Ferroelec. Freq. Control, vol. 45, No. 2, pp. 431-434 (1998).
de Senneville et al., "Real-time adaptive methods for treatment of mobile organs by MRI-controlled high-intensity focussed Ultrasound," Magnetic Resonance in Medicine 57:319-330 (2007).
Fjield et al, "The Combined Concentric-ring and Sector-vortex Phased Array for MRI Guided Ultrasound Surgery," IEEE Trans. on Ultrasonics, Ferroelectrics and Freq. Cont., vol. 44, No. 5, pp. 1157-1167 (Sep. 1997).
Herbert et al., "Energy-based adaptive focusing of waves: application to ultrasonic transcranial therapy," 8th Intl. Symp. on Therapeutic Ultrasound.
Huber et al., "A New Noninvasive Approach in Breast Cancer Therapy Using Magnetic Resonance Imaging-Guided Focussed Ultrasound Surgery," Cancer Research 61, 8441-8447 (Dec. 2001).

International Preliminary Report on Patentability in International Patent Application No. PCT/IB2004/001512, mailed Dec. 8, 2005.
International Search Report and Written Opinion in International Patent Application No. PCT/IB2004/001498, dated Aug. 31, 2004.
International Search Report and Written Opinion in International Patent Application No. PCT/IB2005/002273, mailed Dec. 20, 2005.
International Search Report and Written Opinion in International Patent Application No. PCT/IB2005/002413, mailed Nov. 22, 2005.
International Search Report and Written Opinion in International Patent Application No. PCT/IB2006/001641, mailed Sep. 25, 2006.
International Search Report and Written Opinion in International Patent Application No. PCT/IB2006/003300, mailed Feb. 14, 2008.
International Search Report and Written Opinion in International Patent Application No. PCT/IB2007/001079, mailed Dec. 10, 2007.
International Search Report and Written Opinion in International Patent Application No. PCT/IB2007/002134, mailed Dec. 13, 2007.
International Search Report and Written Opinion in International Patent Application No. PCT/IB2007/002140, mailed Dec. 29, 2008.
International Search Report and Written Opinion in International Patent Application No. PCT/IB2008/003069, mailed Apr. 27, 2009.
Jolesz et al., "Integration of interventional MRI with computer-assisted surgery," J. Magnetic Resonance Imaging. 12:69-77 (2001).
Kohler et al., "Volumetric HIFU Ablation guided by multiplane MRI thermometry," 8th Intl. Symp. on Therapeutic Ultrasound, edited by E.S. Ebbini, U. of Minn. (Sep. 2009).
Kowalski et al., "Optimization of electromagnetic phased-arrays for hyperthermia via magnetic resonance temperature estimation," IEEE Trans. on Biomed. Eng., vol. 49, No. 11, pp. 1229-1241 (Nov. 2002).
Maxwell et al., "Noninvasive thrombolysis using pulsed ultrasound cavitation therapy—Histotripsy," Abstract, U.S. Natl. Lib. of Med., NIH, Ultrasound Med. Biol. (Oct. 23, 2009).
McDannold et al., "MRI evaluation of thermal ablation of tumors and focused ultrasounds," JMRI vol. 8, No. 1, pp. 91-100 (1998).
McDannold et al., "Magnetic resonance acoustic radiation force imaging," Med. Phys. vol. 35, No. 8, pp. 3748-3758 (Aug. 2008).
Medel et al., "Sonothrombolysis: An emerging modality for the management of stroke," Neurosurgery, vol. 65, No. 5, pp. 979-993.
Mougenot et al., "MR monitoring of the near-field HIFU heating," 8th Intl. Symp. on Therapeutic Ultrasound, edited by E.S. Ebbini, U. of Minn. (Sep. 2009).
Partial International Search Report and Written Opinion in International Patent Application No. PCT/IB2007/001079, dated Sep. 25, 2007.
Vimeux et al., "Real-time control of focused ultrasound heating based on rapid MR thermometry," Investig. Radiology, vol. 43, No. 3, pp. 190-193.
Vykhodtseva et al., "MRI detection of the thermal effects of focused ultrasound on the brain," Ultrasound in Med. & Biol., vol. 26, No. 5, pp. 871-880 (2000).
Written Opinion in International Patent Application No. PCT/IL01/00340, mailed Feb. 24, 2003.
Written Opinion in International Patent Application No. PCT/IL02/00477, mailed Feb. 25, 2003.
Written Opinion in International Patent Application No. PCT/IB03/05551, mailed Sep. 10, 2004.
"How is Ablatherm treatment performed?" http://www.edap-hifu.com/eng/physicians/hifu/3c_treatment_treat-description.htm, accessed Jan. 3, 2003.
"What is HIFU? HIFU: High Intensity Focused Ultrasound," http://www.edap-hifu.com/eng/physicians/hifu2a_hifu_overview.htm, accessed Jan. 3, 2003.
"What are the physical principles?" http://www.edap-hifu.com/eng/physicians/hifu/2c_hifu_physical.htm, accessed Jan. 3, 2003.
"How does HIFU create a lesion?" http://www.edap-hifu.com/eng/physicians/hifu/2d_hifu_lesion.htm, accessed Jan. 3, 2003.
"Prostate Cancer Phase I Clinical Trials Using High Intensity Focused Ultrasound (HIFU)," Focus Surgery, http://www.focus-surgery.com/PCT%20Treatment%20with%20HIFU.htm, accessed Jan. 3, 2003.
"Abstract" Focus Surgery, http://www.focus-surgery.com/Sanghvi.htm, accessed Jan. 3, 2003.

Exablate 2000 Specification, InSightec, Ltd. (2 pages).

FDA Approves Exablate 2000 as Non-invasive surgery for Fibroids, Oct. 22, 2004.

International Search Report and Written Opinion in International Patent Application No. PCT/IB2010/000189, mailed Jun. 1, 2010.

International Search Report for PCT/IB03/05551 completion date Mar. 2, 2004 (5 pages).

International Search Report and Written Opinion in Internation Patent Application No. PCT/IB2010/000971, mailed Jul. 29, 2010 (9 pages).

* cited by examiner

TISSUE ABERRATION CORRECTIONS IN ULTRASOUND THERAPY

FIELD OF THE INVENTION

The present invention relates to systems and methods for performing noninvasive procedures using acoustic energy, and, more particularly, to systems and methods for focusing ultrasonic energy through inhomogeneous tissues to treat underlying tissue.

BACKGROUND OF THE INVENTION

Tissue, such as a benign or malignant tumor, within a skull or other region of a body may be treated invasively, e.g., by surgically removing the tissue, or non-invasively, e.g., using thermal ablation. Both approaches may effectively treat certain localized conditions within the brain, but involve delicate procedures in which it is desired to avoid destroying or damaging otherwise healthy tissue. These treatments may not be appropriate for conditions in which diseased tissue is integrated into healthy tissue, unless destroying the healthy tissue is unlikely to affect neurological function significantly.

Thermal ablation, as may be accomplished using focused ultrasound, has particular appeal for treating tissue within the brain and other tissue regions deep within the body, because it generally does not disturb intervening or surrounding healthy tissue. Focused ultrasound may also be attractive, because acoustic energy generally penetrates well through soft tissues, and ultrasonic energy, in particular, may be focused towards focal zones having a cross-section of only a few millimeters due to relatively short wavelengths (e.g., as small as 1.5 millimeters (mm) in cross-section at one Megahertz (1 MHz)). Thus, ultrasonic energy may be focused at a region deep within the body, such as a cancerous tumor or other diseased tissue, to ablate the diseased tissue without significantly damaging surrounding healthy tissue.

To focus ultrasonic energy towards a desired target, a piezoelectric transducer may be used that includes a plurality of transducer elements. A controller may provide drive signals to each of the transducer elements, thereby causing the transducer elements to transmit acoustic energy such that constructive interference occurs at a "focal zone." At the focal zone, sufficient acoustic energy may be delivered to heat tissue within the focal zone until tissue necrosis occurs, i.e., until the tissue is destroyed. Preferably, tissue along the path through which the acoustic energy passes ("the pass zone") outside the focal zone, is heated only minimally, if at all, thereby minimizing damaging tissue outside the focal zone.

As acoustic energy passes through tissue, the acoustic energy may interact with the tissue through multiple processes: propagation, scattering, absorption, reflection, and refraction. The intensity of the acoustic energy transmitted by the transducer array generally determines the therapeutic effectiveness, i.e., the volume of tissue destroyed within the focal zone (although there may be some losses as the acoustic energy interacts with intervening tissue between the transducer and the focal zone). The size of the focus zone may also depend upon system parameters, such as transducer element characteristics, frequency of the acoustic energy, and focal depth (the distance from the transducer to the focal zone), as well as patient-related parameters, such as tissue inhomogeneity.

When a transducer is activated, the relative phase of drive signals delivered to each transducer element may be adjusted based upon the distance of the respective transducer element from the focal zone. Generally, an average speed of sound is used to approximate the speed at which the acoustic energy passes through tissue, e.g., 1540 meters per second (m/s), and to predict the location of the focal zone.

While system parameters are generally fixed for a given transducer array, tissue homogeneity may vary significantly from patient to patient, and even between different tissue regions within the same patient. Tissue inhomogeneity may decrease intensity of the acoustic energy at the focal zone and may even move the location of the focal zone within the patient's body. Specifically, because the speed of sound differs in different types of tissue, as portions of a beam of acoustic energy travel along different paths towards the focal zone, they may experience a relative phase shift or time delay, which may change the intensity at the focal zone and/or move the location of the focal zone.

For example, the speed of sound through fat is approximately 1460 meters per second (m/s), while the speed of sound through muscle is approximately 1600 meters per second (m/s). The speed of sound through bone tissue is much faster, for example, approximately 3000 meters per second (m/s) for skull bone tissue. The speed of sound also varies in different organs. For example, the speed of sound in brain tissue is approximately 1570 meters per second (m/s), approximately 1555 meters per second (m/s) in the liver, and approximately 1565 meters per second (m/s) in the kidney.

Since a beam of acoustic energy has a relatively wide aperture where it enters the body, different parts of the acoustic energy may pass through different tissue pass zones, and therefore may pass through different tissue types. Thus, when acoustic energy is transmitted through tissue, portions of the acoustic energy may experience different speeds of sound, which may shift the relative phases of acoustic energy transmitted from respective transducer elements. This phase shifting may decrease the constructive interference of the acoustic energy at the focal zone, which may reduce the effectiveness of the treatment, or may even move the focal zone in an unpredictable manner. For example, a layer of fat that is only seven millimeters (7 mm) thick within muscle tissue may introduce a phase shift of 180° at an ultrasonic frequency of one Megahertz (1 MHz), which would change desired constructive interference at the focal zone into destructive interference.

Tissue inhomogeneity may also cause refraction of acoustic energy at the boundaries of tissue regions having different speeds of sound. Refraction may decrease constructive interference, and hence, the intensity of the acoustic energy at the focal zone, particularly when the acoustic energy passes through bone. Thus, inhomogeneous tissue structures may generate beam aberrations and refractions, which may distort the focus and reduce the intensity, thus affecting treatment efficiency.

Accordingly, systems and methods for effectively focusing acoustic energy towards a desired focal zone would be useful.

SUMMARY OF THE INVENTION

The present invention is directed to systems and methods for performing noninvasive procedures using acoustic energy, and, more particularly, to systems and methods for focusing ultrasonic energy through inhomogeneous tissue to treat underlying tissue.

In accordance with one aspect of the present invention, a system is provided for delivering acoustic energy through intervening tissue into a target site within a tissue region. The system may include a transducer array including a plurality of transducer elements configured for transmitting acoustic energy, e.g., ultrasonic energy, along respective pass zones through the intervening tissue towards the target, site.

The system may include an imager for imaging the tissue region, the imager generating image data including tissue types of the intervening tissue. In exemplary embodiments, the imager may be a magnetic resonance imager, a computer tomography imager, or an ultrasound imager. The imager may generate one or more images including intensity data that include a relative density of respective tissue types. The imager may generate a plurality of two-dimensional images including the intervening tissue, e.g., image slices, or may generate one- or three-dimensional images.

A processor is coupled to the imager for receiving image data to determine boundaries between a plurality of tissue types within the intervening tissue and generate respective correction factors for the transducer elements to compensate for refraction occurring at the boundaries between the tissue types within the respective pass zones. In addition or alternatively, the respective correction factors may compensate for variations in speed of sound of the tissue types within the respective pass zones.

In one embodiment, the processor may be configured for converting a plurality of two-dimensional images into one or more three-dimensional renderings including the intervening tissue. The processor may automatically determine the boundaries between different tissue types within the intervening tissue based upon the three-dimensional rendering(s). For example, the image data may include intensity data that may identify a relative density of respective tissue types, and the processor may be configured for analyzing the intensity data to identify regions including different tissue types. Once the regions of different tissue types are identified, the processor may be configured for automatically determining the boundaries between the identified regions of different tissue types, and generating the correction factors.

Alternatively, the system may include a display for displaying the three-dimensional rendering(s) and/or the two-dimensional images, and a user interface for interacting with the rendering(s) and/or images to identify tissue types within the intervening tissue manually. In a further alternative, the processor may be configured for automatically determining the boundaries between the plurality of tissue types based upon two-dimensional images acquired by the imager.

In addition, the system may include a controller coupled to the processor and the transducer array that may be configured for receiving the correction factors from the processor and providing excitation signals to the transducer elements based upon the correction factors. For example, the correction factors may include phase correction factors associated with respective transducer elements, and the controller may include a phase adjuster for adjusting phases of excitation signals provided to the transducer elements based upon the phase correction factors, which is required in continuous wave mode. Alternatively, the processor may be configured to adjust transmit time of respective transducer elements which may be required in pulse transmission mode. In addition or alternatively, the excitation factors may include amplitude correction factors associated with the transducer elements, and the controller may include one or more amplifiers for amplifying the excitation signals provided to the transducer elements based upon the amplitude correction factors.

In accordance with another aspect of the present invention, a method is provided for focusing acoustic energy transmitted from a plurality of transducer elements of a transducer array through intervening tissue into a target site within a tissue region. In a preferred embodiment, the target site is a tumor or other tissue structure within a brain, and the intervening tissue may include skull bone tissue, skin, and/or dura matter. In addition or alternatively, the target site may be a tumor or other tissue structure within soft tissue, and the intervening tissue may include, bone, fat, muscle, and/or organ tissue.

One or more images may be acquired of a portion of the tissue region that includes the intervening tissue and the target site. For example, the one or more images may include a plurality of image slices selected from magnetic resonance images, computer tomography images, and/or ultrasound images of the tissue region.

Boundaries may be determined between different tissue types within the intervening tissue from the one or more images. In one method, one or more three-dimensional renderings may be volumetrically reconstructed of the tissue region from the image slices. Regions of different tissue types within the tissue region may be identified based upon the three-dimensional rendering, and three-dimensional boundaries between the identified regions of different tissue types may be identified within the tissue region. This process may be performed automatically by a processor or controller, manually by an operator, or by a combination of manual and automatic procedures.

In addition or alternatively, the images of the tissue region may include intensity data that identify a relative density of different tissue types. The intensity data may be analyzed directly to identify regions including the plurality of tissue types and/or may be reconstructed into one or more three-dimensional renderings before being analyzed. Once the tissue types are identified, the boundaries between the identified regions of different tissue types may be determined.

Respective excitation correction factors may be generated for each transducer element of the transducer array to compensate for variations in speed of sound of the tissue types within pass zones extending from respective transducer elements through the intervening tissue towards the target site and/or to compensate for refraction occurring at the boundaries between the tissue types within the pass zones.

The transducer elements may then be driven with excitation signals based, at least in part, upon the excitation correction factors, thereby focusing acoustic energy from the transducer array at the target site. The excitation correction factors may be generated to correct for displacement of a focal zone of the transducer away from the target site and/or to correct for defocusing of the focal zone at the target site. Preferably, sufficient acoustic energy is focused at the target site for sufficient time to ablate tissue at the target site, as is well known in the art.

In one embodiment, the excitation correction factors may include phase shift factors, and the step of generating excitation correction factors may include generating the phase shift factors, at least in part, by conducting ray calculations. The ray calculations may be based upon hypothetical rays extending from each transducer element to the target site (forward ray calculations) and/or from the target site to each transducer element (reverse ray calculations).

Alternatively, the excitation correction factors may include time delays, and the excitation correction factors may be generated by determining a respective propagation time along a pass zone extending from each transducer element through boundaries between successive tissue types and the target site. The propagation time may be based, at least in part, upon the speed of sound in the successive tissue types, refraction at the boundaries between the successive tissue types, and/or a distance of a resultant path (the pass zone) between the respective transducer element and the target site.

In accordance with another aspect of the present invention, a method is provided for focusing acoustic energy to ablate a target site within a tissue region with a transducer array comprising a plurality of transducer elements. One or more images may be acquired of the tissue region that includes the target site and intervening tissue between the transducer array and the target site. Boundaries may be determined between a plurality of tissue types within the intervening tissue based upon the one or more images, e.g., using the systems and methods described above. Correction factors may be generated for each transducer element of the transducer array to compensate for refraction occurring at the boundaries between the tissue types within pass zones extending from respective transducer elements through the intervening tissue to the target site and for variations in speed of sound of the tissue types within the pass zones. The transducer elements may be driven with excitation signals based, at least in part, upon the correction factors to focus acoustic energy from the transducer elements at the target site for sufficient time to ablate tissue at the target site.

In one embodiment, the correction factors may include phase correction factors associated with respective transducer elements, and the phases of excitation signals provided to the respective transducer elements may be adjusted based upon the phase correction factors. In addition or alternatively, the excitation factors may include amplitude correction factors associated with respective transducer elements, and the excitation signals provided to the respective transducer elements may be amplified based upon the amplitude correction factors.

Other objects and features of the present invention will become apparent from consideration of the following description taken in conjunction with the accompanying drawings.

DETAILED DESCRIPTION OF THE PREFERRED EMBODIMENTS

Figure 1:
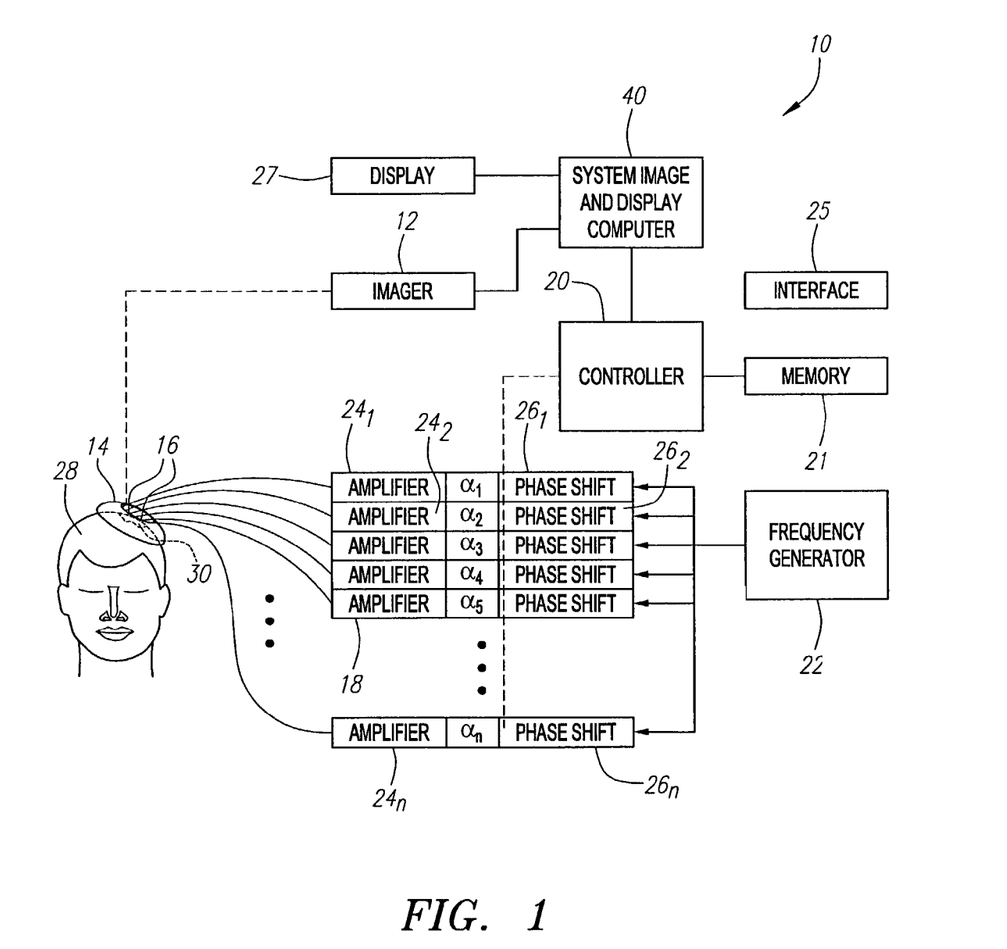
FIG. 1 is a schematic diagram of an ultrasound therapy system, in accordance with the present invention.

Turning to the drawings, FIG. 1 shows a preferred embodiment of a focused ultrasound system 10, in accordance with the present invention, that includes an imager 12, an acoustic transducer 14, a beam former or signal adjuster 18, a controller 20, a frequency generator 22, and a system image and display computer 40. Optionally, the system 10 may also include a user interface 25, such as a touch screen, a keyboard, and/or a mouse (not shown), and/or a display 27. The system 10 may determine characteristics within a skull 28 of a patient 30 and/or may deliver acoustic energy to tissue within the skull 28, as explained further below. Preferably, the system is configured for delivering ultrasonic energy, e.g., between ten kilohertz (0.01 MHz) and ten Megahertz (10 MHz) to tissue within the skull 28 or other tissue region.

The transducer 14 includes a plurality of "n" transducer elements 16 ("n" being an integer greater than one), thereby providing a multiple element transducer array. The transducer 14 may include a flexible or semi-rigid base or panel that may conform to the shape of the skull 28. The transducer 14 may be pre-curved (e.g. biased to a spherical or other concave shape), as shown in FIG. 1, such that the transducer 14 may be placed on or near a portion of a skull 28. Alternatively, the transducer 14 may be planar, parabolic, or any other suitable shape, e.g., circular, elliptical, and the like.

The transducer elements 16 may be mounted to or otherwise arranged on the base of the transducer 14 in a predetermined pattern. For example, the transducer elements 16 may be arranged substantially symmetrically about a central axis or in an orthogonal grid pattern (not shown). The transducer elements 16 may be mounted in silicone rubber or any other material suitable for dampening any mechanical coupling between the transducer elements 16. In an exemplary embodiment, the transducer elements 16 may be one square centimeter (1 $cm^2$) piezoelectric ceramic elements. Other materials may also be used; for example, the transducer elements 16 may be formed from one or more pieces of piezo-composite material or other material that converts electrical energy to acoustic energy. To help assure maximum power transfer to the transducer elements 16, the transducer elements 16 may be configured for electrical resonance at a specific frequency or number of frequencies such that loads to amplifiers $24_i$ are mainly resistive.

The transducer elements 16 of the transducer 14 are electrically coupled to the signal adjuster 18, which is, in turn, electrically coupled to the frequency generator 22. The frequency generator 22 may provide a common radio frequency (RF) signal as an input signal to the signal adjuster 18. The frequency generator 22 may be any type of generator capable of producing appropriate signals for the signal adjuster 18. Together, the frequency generator 22 and signal adjuster 18 drive the individual transducer elements 16 with excitation signals such that the transducer elements 16 transmit acoustic energy. Preferably, the excitation signals provided to each of the transducer elements 16 have the same frequency, but may have different phases and/or amplitudes in order to transmit acoustic energy through the skull 28 and focus the energy at a selected region within the skull 28, i.e., within the patient's brain (not shown).

Signals may be provided to the transducer elements 16 of the transducer 14 by a driving arrangement similar to that reported in Daum et al., "Design and Evaluation of a Feedback Based Phased Array System for Ultrasound Surgery," IEEE Trans. Ultrason. Ferroelectr. Freq. Control 45(2):431-4, 1998, the disclosure of which is expressly incorporated herein by reference, but with a driving frequency selected between about one hundred kilohertz (100 kHz) and about ten Megahertz (10 MHz). The power and phase to each transducer element 16 may be manually controlled or automatically controlled using software and feedback.

Preferably, the signal adjuster 18 includes a plurality of "n" amplifiers $24_1$-$24_N$ and "n" phase shifters $26_1$-$26_n$ (where "n" corresponds to the number of transducer elements 16 coupled to the signal adjuster 18) that are coupled in respective sets of amplifiers 24 and phase shifters 26. The input signal from the frequency generator 22 is split such that each of the phase shifters 26 receives the signal from the frequency generator 22. Each phase shifter 26 and amplifier 24 set represents a channel of the signal adjuster 18 that is coupled to a respective transducer element 16. The phase shifters 26 may adjust the phase of the incoming signal from the frequency generator 22 by respective phase shift factors $\alpha_1$-$\alpha_n$. Preferably, the phase shifters 26 provide approximately one degree precision (8-bit resolution), although lower phase resolution may be adequate for many applications.

The amplifiers 24 amplify the signals from the phase shifters 26 to provide amplified excitation signals to the transducer elements 16, e.g., via coaxial cables or other connections, which may individually connect the amplifiers 24 and respective transducer elements 16. Optionally, individual transducer elements 16 may be switched off (set to an amplitude of zero) if the pass zones of the respective transducer elements include air pockets, if the beam incidence angle is too low, or in light of other factors. An internal power meter (not shown) in the signal adjuster 18 may monitor power supplied by the amplifiers 24.

The phase shift factors $\alpha_1$-$\alpha_n$ of the phase shifters 26 allow the acoustic energy transmitted by the transducer elements 16 to be steered, i.e., allow the "focal zone" (the region in space towards which the acoustic energy is focused) to be moved, e.g., along a "z" axis (an axis extending orthogonally from the transmission surface of the transducer 14 into the skull 28, not shown) and/or along the "x" or "y" axes. The component of each phase shift factor associated with steering may be computed using known techniques, e.g., using average speed of sound in the body and the distance from each transducer element 16 to a target site of interest (the intended focal zone within a tissue region).

In addition, the phase shift factors may also compensate for phase distortion of the ultrasonic energy transmitted by each transducer element 16 that is caused when the acoustic energy passes through tissue within the skull 28. The component of each phase shift factor $\alpha_1$-$\alpha_n$ associated with phase distortion may compensate for perturbations and distortions introduced by the bone of the skull, the skin/skull interface, the dura matter/skull interface, by variations in skull thickness, and/or by structural considerations such as air-filled or liquid-filled pockets in the skull 28 (all not shown). The two components that make up the phase shift factors $\alpha_1$-$\alpha_n$, i.e., the steering components and the phase distortion components, are summed to determine the composite phase shift factors $\alpha_1$-$\alpha_n$ for the respective channels in order to focus ultrasonic energy at a desired steering angle relative to the "z" axis and at a desired distance ("focal distance") from the transducer 14.

The phase shift factors $\alpha_1$-$\alpha_n$ are determined by the system image and display computer 40, which may be coupled to the controller 20 and to the imager 12. Alternatively, the controller 20 itself may include all of the hardware components and/or software modules necessary to determine the phase shift factors $\alpha_1$-$\alpha_n$, instead of the separate computer 40. The system image and display computer 40 may include one or more software modules, hardware components, firmware, hardwiring, or any combinations of these. For example, the system image and display computer 40 may be a general or special purpose digital data processor programmed with software in a conventional manner to generate the phase shift factors $\alpha_1$-$\alpha_n$, which may be transferred to the controller 20 for subsequent transfer to the phase shifters 26 or directly to the phase shifters 26 based upon images received from the imager 12.

The system image and display computer 40 may determine the phase shift factors $\alpha_1$-$\alpha_n$ by automatically analyzing images and identifying tissue characteristics of interest from the images. Sufficient information is provided by the imager 12 to the system image and display computer 40 to determine the phase shift factors $\alpha_1$-$\alpha_n$. Alternatively, a user may manually analyze the images and identify tissue characteristics, or a combination of automatic and manual analysis may be used.

First, the imager 12 may obtain images of the interior of the skull 28 from which boundaries of the skull bone tissue, and optionally other tissue regions therein, may be determined. For example, the imager 12 may be a Magnetic Resonance Imaging (MRI) device, a Computer Tomography (CT) device, or an Ultrasound Imaging (UIS) device (not shown). The images may be one-dimensional images or preferably two-dimensional images of sectional planes through the site of interest. Alternatively, three-dimensional images may also be received from the imager 12. If the imager 12 is a CT device, the imager 12 may determine and provide a CT number (also called a Hounsfield number) for each pixel in images provided by the imager 12. Exemplary embodiments of systems and methods for acquiring images using an ultrasound probe are disclosed in U.S. application Ser. No. 10/190,787, filed on Jul. 8, 2002, and entitled "Image-Based Tissue Aberration Corrections in Ultrasound Imaging, the disclosure of which is expressly incorporated herein by reference.

The system image and display computer 40 may generate a three-dimensional rendering of the skull 28 from images received from the imager 12 and determine the skull bone tissue boundaries from the three-dimensional rendering. For example, the system image and display computer 40 may divide the three-dimensional rendering into "voxels" (volume pixels of the three-dimensional image). Tissue boundaries of the imaged tissue may then be determined based upon the three-dimensional renderings, as explained below. Alternatively, the tissue boundaries may be determined and/or inferred from two-dimensional images. The images received from the imager 12 and/or the three-dimensional rendering may also be displayed on display 27 for review and/or analysis by a physician, technician, or other operator.

Figure 2:
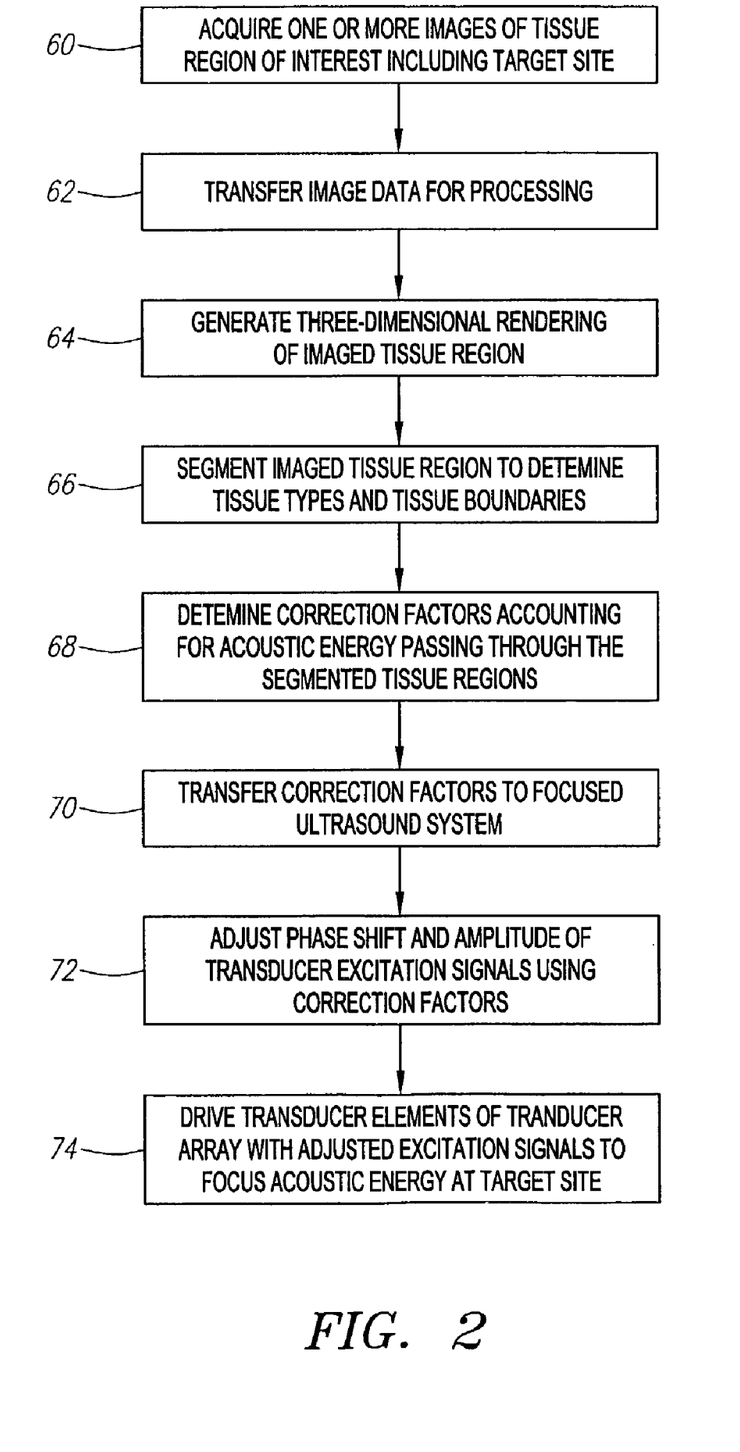
FIG. 2 is a flow diagram of a method for determining excitation correction factors and driving transducer elements using the determined factors, in accordance with the present invention.

Turning to FIG. 2, an exemplary procedure for analyzing images of a tissue region to be treated is shown, e.g., to control delivering therapeutic energy to a target site within the tissue region. Preferably, the method is used in conjunction with focused ultrasound therapy, i.e., involving a multiple element transducer array that is placed adjacent the tissue region and used to deliver acoustic energy into the tissue region to the target site. In an exemplary embodiment, the tissue region is a patient's skull, and the target site is a tumor or other tissue structure within the patient's brain.

At step 60, an imager, such as the imager 12 shown in FIG. 1, may acquire one or more images of the target region, e.g., the interior of the patient's skull. As explained above, the imager may be any of a variety of imaging devices, such as an MRI device, a CT device, or an ULS device. The images are at least one-dimensional, e.g., a plurality of vectors, and preferably are two-dimensional, e.g., a plurality of spaced-apart image planes or "slices" through the tissue region of interest. For example, the tissue region may be a skull, and the images may be multiple slices through the skull that may be used to identify a tumor or other tissue structure within the patient's brain.

At step 62, image data representing the images are transferred to a processor, such as the system image and display computer 40 shown in FIG. 1. In one embodiment, the imager 12 and the system image and display computer 40 may be directly coupled to one another, i.e., may be at the same location. In an alternative embodiment, the imager 12 (and consequently the patient 30) may be at one location, and the image data from the imager 12 may be transferred to a remote system image and display computer 40, which may receive data from multiple imagers (not shown). Such transfer may be over any wire or wireless network, such as a telephonic network or the Internet. Thus, a central system image and display computer 40 may exchange data with multiple remote sites, e.g., hospitals or other treatment facilities.

The transfer of image data may occur immediately upon acquiring the images from the patient, for example, if the patient is undergoing treatment. Alternatively, the image data may be stored at the imager location, e.g., in memory or on a compact disc (CD) or other portable storage device. Thus, a set of reference images may be obtained of the tissue region at some time before performing the treatment. The transfer may be completed automatically or may occur only upon instruction from a physician or other operator.

Once the processor, e.g., the system image and display computer 40, has received the image data, the image data may be manipulated to generate one or more three-dimensional renderings and/or to generate treatment parameters. For example, at step 64, a three-dimensional rendering of at least some tissues within the tissue region may be generated, which may be segmented into tissue types. This analysis may include a pass zone, i.e., a portion of the tissue region disposed between the transducer being used to treat the patient and the tissue structure targeted for treatment. Preferably, the analysis includes the pass zones of each transducer element of the transducer array, i.e., the paths that acoustic energy travels from respective transducer elements through intervening tissue to the target site. The three-dimensional rendering may be interpolated from multiple two-dimensional images, e.g., to fill in gaps between adjacent spaced-apart image slices, thereby creating a three-dimensional image that may be used for subsequent analysis. Alternatively, two-dimensional images may be analyzed directly.

At step 66, the three-dimensional rendering(s) (or alternatively, two-dimensional images) may be segmented and classified into tissue types, e.g., to determine the boundaries between the different tissue types within the imaged tissue region. The rendering(s) or image(s) may be defined by individual "voxels" (volume pixels of a three-dimensional image or area pixels of a two-dimensional image). Each voxel in the image may be mapped automatically into a location data set and correlated to a tissue type. For example, each voxel may be assigned coordinates identifying its location in space, e.g., (X,Y) for a two-dimensional location data set and (X,Y,Z) for a three-dimensional location data set, and a tissue type (T), resulting in a data set including (X, Y, T) or (X, Y, Z, T) coordinates for each voxel.

The processor, such as the system image and display computer 40, may automatically determine the tissue types using known algorithms. For example, intensity of portions of the images received from the imager (or the three-dimensional rendering itself) may be correlated to different tissue types using methods well known in the art, such as anatomical template matching. Alternatively, an operator may review the rendering(s) and/or image(s) to identify the different tissue types to be assigned to the individual voxels.

Given the voxel data sets, segmentation may then be performed, e.g., to determine the boundaries between one or more different tissue types within the tissue region imaged in the image data. In the example where the tissue region is a patient's skull, this may include determining boundaries between layers of tissue within the skull bone itself, between the skin/skull interface, and/or between the dura matter/skull interface.

This procedure may be automatic, semi-automatic, or manual. For example, a physician or other operator may review the rendering(s) and/or image(s) on a display and manually segment them by tracing boundaries between one or more like tissue types, by changing thresholds, and the like. A suitable interface device, such as a touch screen or a mouse controlling a pointer on a display showing the rendering(s) or image(s), may be used to identify and connect like tissue types.

In a semi-automatic segmentation technique, an expanding area algorithm may be used to fill each region of the rendering(s) and/or image(s) designated by a user based upon intensity variations in the image. For example, clicking on a mouse while a pointer is located within a portion of an image having a first intensity or identified tissue type may execute the expanding area algorithm to fill an entire region having like intensity or tissue type to the portion identified with the pointer. Alternatively, a fully automatic segmentation algorithm may be used to segment each tissue region based upon intensity variations or other classified parameters in the image.

If two-dimensional images are segmented, one or more three-dimensional renderings or images of the tissue region may be interpolated from a plurality of spaced-apart two-dimensional images upon completing segmentation. The number of two-dimensional images necessary to interpolate an effective three-dimensional rendering may depend on the geometrical rate of change of the tissue region and the desired accuracy of the interpolation, as will be appreciated by those skilled in the art.

At step 68, correction factors may be determined based upon the two- or three-dimensional rendering(s) or image(s), which may be used to assist subsequent treatment of the tissue region. Exemplary systems and methods for determining these correction factors are disclosed in U.S. application Ser. No. 09/738,514, filed Dec. 15, 2000, the disclosure of which is expressly incorporated herein by reference. In one embodiment, the correction factors account for different speeds of sound that may be encountered by acoustic energy passing through different tissue types in respective segmented tissue regions. In addition or alternatively, the correction factors may account for refraction of acoustic energy that may occur at boundaries of the segmented tissue regions, as explained further below.

The resulting correction factors, e.g., phase shift factors and/or amplitude factors, may be used to assist a particular course of treatment, preferably focusing acoustic energy at a target site within the imaged tissue region. For example, at step 70, the correction factors may be transferred to a focused ultrasound system, such as the controller 20, signal adjuster 18, and transducer 14 shown in FIG. 1.

At step 72, the focused ultrasound system may use the correction factors to control a beam former or signal adjuster, such as the signal adjuster 18 shown in FIG. 1, which delivers excitation or drive signals to the transducer based upon the correction factors. For example, with continued reference to FIG. 1, one or more base signals may be supplied to a signal adjuster 18, e.g., by a frequency generator 22, as described above. The base signal(s) may be split into a plurality of channels, preferably into individual channels corresponding to respective transducer elements 16 of the transducer 14. The phase of the signals for the respective channels may be adjusted by the signal adjuster 18 according to phase correction factors received by the controller 20. For example, the phases may be adjusted to compensate for acoustic energy from respective transducer elements 16 passing through different tissue types and/or encountering one or more tissue boundaries. This may be in addition to other phase adjustments provided to focus the acoustic energy at a particular location or in a particular shape focal zone or to compensate for transducer element variations, as is known to those skilled in the art. The phase-adjusted signals may be amplified based upon amplitude correction factors, e.g., by amplifiers 24, which may amplify the excitation signals. Alternatively, the signals for the respective channels may be amplified before they are phase-adjusted.

At step 74, the amplified and phase-adjusted excitation signals may be delivered to the transducer 14 to drive the respective transducer elements 16. The transducer elements 16 convert the excitation signals into acoustic energy that is transmitted from the respective transducer elements 16 of the transducer 14 into the imaged tissue region of the patient 30, i.e., through any intervening tissue to a target site within the tissue region, e.g., within a skull 28.

During the treatment, images may be acquired, e.g., using the same imager that acquired the reference image data, to monitor the progress of the treatment. For example, the images may be transferred to a processor, such as the system image and display computer 40 of FIG. 1, for real time or nearly real time monitoring. The acquired treatment images may be compared with the previously acquired reference images. If necessary, the treatment parameters may be adjusted, e.g., by providing further amplitude and/or phase correction factors, to modify the energy delivered to the tissue region and reflect events as they unfold, e.g., using the same procedures described above, thereby transforming the treatment into a controlled process.

Figure 3:
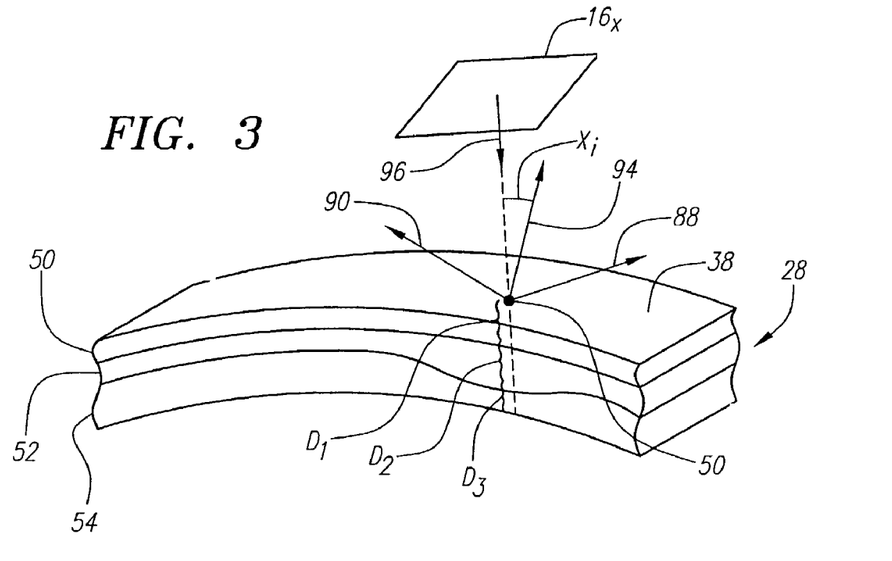
FIG. 3 is a perspective cross-sectional view of a portion of a patient's skull.

Turning to FIG. 3, a method shall be described for determining the excitation correction factors to compensate for phase shifting of acoustic energy passing through skull tissue where the acoustic energy is normal or nearly normal to the boundaries of the tissue. As shown, the skull 28 includes two layers 50, 54 of cortical bone and an intermediate layer 52 of trabecular bone. A transducer element $16_x$ is shown adjacent the skull 28 that may emit acoustic energy into the skull 28 in a direction of propagation identified by a vector 96 intersecting the skull at point $r_0$. From a three-dimensional rendering of the skull 28, two perpendicular vectors 88, 90 may be determined that extend along the surface 38 of the skull 28 from the point of interest $r_0$ on the skull's surface 38 in the x and y directions, respectively, or other imaging coordinate system. The vectors 88, 90 may be used to calculate a vector 94 that is normal to the surface 38 using known methods. A scalar product may be calculated of the vector 94 and the vector 96 identifying the incident angle:

(1)

Thicknesses, $D_1$, $D_2$, $D_3$, of each layer 50, 52, 54, respectively, are obtained, using intensity variations, starting at a location on the skull surface $r_0=(x_0, y_0, z_0)$ and continuing to a point on the next layer 52 where $r=(x, y, z)$, $$r = r_0 + Dn. \quad (2)$$

This process is repeated between the sequential layers starting at the entry surface to layer n to the entry surface to the next layer. The above discussion assumes near-normal propagation through the skull bone, and assumes that the different layers of skull bone tissue 50, 52, 54 are each homogenous. Treating each of the layers 50, 52, 54 as a single layer for purposes of ultrasound propagation speed, a simple relation may be used to express the phase shift due to propagation through a given point on the skull:

$$\phi = 360 f D \left( \frac{1}{c_0} - \frac{1}{c_s} \right) \quad (3)$$

where f is the driving frequency, $c_0$ is the average speed of sound in tissue, $c_s$ is the speed of sound in skull bone tissue, and D is the thickness of the skull.

Tissue inhomogeneity may cause refraction that alters the path, and hence the distance traveled by the ultrasonic energy traveling along the path. The phase of the ultrasonic energy transmitted by the transducer element at the focal zone may thereby be further shifted, which may decrease the constructive interference and hence the intensity of the ultrasonic energy delivered to the focal zone.

If near normal propagation is not assumed (as it was with respect to FIG. 3), refraction of the ultrasonic energy at one or more boundary layers may be considered in determining the excitation factors (as indicated in step 68 of FIG. 2) for the transducer elements, so that constructive interference of the ultrasonic energy at the focal zone is maximized.

Ultrasonic beam refraction is described by Snell's law:

$$\frac{\sin\theta_1}{\sin\theta_2} = \frac{C_1}{C_2} \quad (4)$$

where $\theta_1$, $\theta_2$ are the angles between the normal to the surface and the incident and refracted rays in the respective tissue regions and $C_1$, $C_2$ are the speeds of sound in the respective tissue regions. Because refraction at the boundary between soft tissue and bone may be significant, consideration of refraction to correct tissue aberration may be particularly useful in treating the brain with ultrasonic energy.

Figure 4:
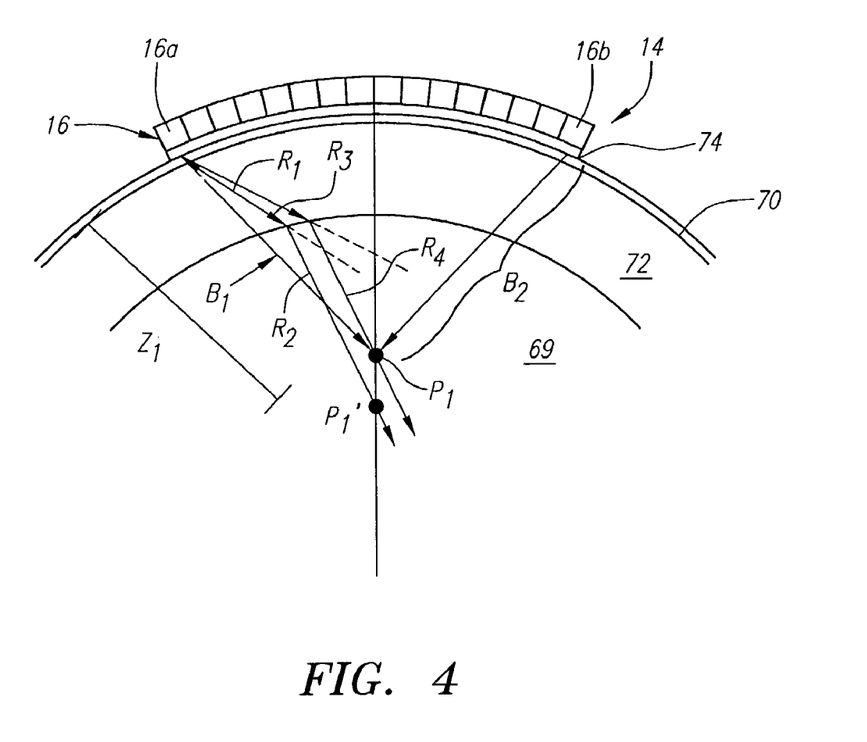
FIG. 4 is a cross-sectional view of a patient's skull, showing representative rays of ultrasonic energy refracting as they are transmitted through the skull.

FIG. 4 is a cross-sectional view of a pass zone Z1 that extends between a transducer array 14 and a target region (as identified by the focal zone P1), which may be a tumor or other tissue structure within brain tissue 69. In this simplified illustration, the transducer array 14 includes one row of transducer elements 16 and is placed adjacent to the patient's skin 70 over the skull bone tissue 72. A layer of coupling material 74, e.g., water or acoustic gel, may be provided between the transducer array 14 and the skin 70, as shown, to improve acoustic coupling between the transducer 14 and the skin 70.

As discussed above, skull bone tissue 72 typically includes an intermediate layer of trabecular bone between two layers of cortical bone. Trabecular bone and cortical bone have different densities, which vary their respective speeds of sound. As a first approximation, however, the skull bone tissue 72 may be considered to be homogenous and an average speed of sound in skull bone tissue of three thousand meters per second (3000 m/s) may be used for the entire bone tissue region 72. Alternatively, the multiple layers of bone tissue within the skull 72 may be segmented (not shown) and the speeds of sound and the distance traveled through each segmented region may be separately considered in accordance with the teachings of the present invention, if desired or necessary to improve focus spatial peak power (the maximum power intensity of acoustic energy delivered to the focal zone).

With continued reference to FIG. 4, if there were no refraction through the tissue, exemplary transducer elements 16*a*, 16b on the transducer array 14 would transmit acoustic energy directly focused on an intended focal zone P1, as represented by rays B1, B2, respectively. Because the acoustic energy may refract at (at least) two locations, i.e., the boundary between the skin 70 and the bone 72 and the boundary between the bone 72 and the brain tissue 69, these rays may not reflect the actual path followed by the acoustic energy transmitted by the transducer elements 16a, 16b. It is noted that acoustic energy that is normal to a boundary of a tissue region will not be refracted by the boundary.

For example, ray R1 may represent an actual path that may result from the acoustic energy transmitted by transducer element 16a due to refraction at the boundary between the skin tissue 70 and the bone tissue 72. Ray R2 may then represent the actual path of the acoustic energy passing through the brain tissue 69 to actual focal zone P1' due to refraction at the boundary between the bone tissue 72 and the brain tissue 69. Because of refraction, the acoustic energy may travel a different distance than predicted, and therefore may shift the phase of the acoustic energy from an expected value at the focal zone P1 to an actual value as a result of the new path from transducer element 16a to the focal zone P1 (as a clarification, in phased arrays the focal point is defined by the electronic phase map that is feeding the elements. In the case of FIG. 4., a different phase map will shift the focus from $P_1'$ back to $P_1$, as explained below using rays R3, R4).

To compensate for refraction that may be caused by tissue inhomogeneity, one or more ray calculations may be performed between the transducer elements 16 and the intended focal zone P1, taking into consideration refraction of the acoustic energy transmitted by the respective transducer elements 16. For example, FIG. 4 shows rays R3, R4, which represent the necessary path of travel to focus acoustic energy transmitted by the transducer element 16a at the focal zone P1 taking into account the refraction. These rays may be interpolated from a forward calculation, i.e., determining the path of acoustic energy from the point of transmission at the respective transducer element 16 through the various tissue regions encountered until a desired phase shift is achieved at the focal zone to create the desired constructive interference. Alternatively, a reverse ray calculation may be performed, beginning at the focal zone P1 through the various tissue regions to the respective transducer element 16. These ray calculations take into consideration Snell's Law, as explained above with reference to Equation 4, as will be appreciated by those skilled in the art.

The length of each ray, which corresponds to the distance traveled by the acoustic energy transmitted by the respective transducer element may then be computed. For example, a distance L3 of ray R3 extending through the skull bone tissue 72 may be computed by identifying the voxel coordinates on the boundaries intercepted by the ray R3. If the segmented boundary between the skin 70 and the skull bone tissue 72 has voxel coordinates (Xa, Ya, Za) and the segmented boundary between the skull bone tissue 72 and the brain tissue 69 has voxel coordinates (Xb, Yb, Zb), then the distance L3 traversed by the ray R3 between the boundaries is:

$$L3 = ((Xa-Xb)^2 + (Ya-Yb)^2 + (Za-Zb)^2)^{1/2}. \quad (5)$$

The distance L3 in Equation 5 may be used to determine the phase shift caused by the skull bone tissue 72 and determine the necessary phase shift factors $\alpha_1$-$\alpha_n$.

The brain tissue 69 may also cause a phase shift in the acoustic energy due to the difference between the average speed of sound in body tissue typically used to determine the phase shift factors $\alpha_1$-$\alpha_n$ and the actual speed of sound in brain tissue 69. The distance L4 traveled by the second ray R4 through the brain tissue 69 to the focal zone P1 may be computed for further phase shift correction, based on the voxel coordinates of the boundary between the skull bone tissue 72 and the voxel coordinates of the focal zone P1.

Acoustic energy used in ultrasound therapy is typically continuous waves, rather than discrete rays, but the use of rays should adequately represent the waves themselves to allow reasonably accurate calculations to be performed. Since transducer elements have a finite size, improved accuracy may be achieved by using multiple rays per element, calculating the required phase for each ray and using the average phase for the element. The result may be an iterative process, whereby hypothetical rays are projected through the boundaries of the successive tissue layers until appropriate correction factors are determined that position the focal zone of the acoustic energy at the target site.

Excitation correction factors may be computed using either phase or timing. In the case of transmission timing control instead of computing phase shift factors, the excitation correction factors may be based on actual propagation times for the refracted acoustic energy passing through the one or more segmented tissue regions. The actual propagation times may be used to determine corrected transmissions times for each of the transducer elements 16 so that the acoustic energy transmitted by the transducer elements 16 constructively interferes at the focal zone P1.

The propagation time T of ray R through a tissue region is:

$$T = \frac{L}{V} \text{Sec}, \quad (6)$$

where V is the speed of sound through the tissue (e.g., three thousand meters per second (3000 m/s) for skull bone tissue) and L is the length of a ray R in the tissue, i.e., the distance that the representative ray would travel through the tissue region.

In the example described above with respect to FIG. 4, when conducting focused ultrasound therapy in the brain 69 using a transducer 14, the actual trajectory and derived propagation time of acoustic energy from respective transducer elements may be determined. For example, the propagation time for acoustic energy from transducer element 16a to pass through the skull bone 72, as represented by ray R3, may be determined using the speed of sound through the bone tissue, e.g., three thousand meters per second (3000 m/s) and used to compute corrective delay times. For phase correction due to passage through the brain tissue 69, the propagation time for representative ray R4 may be determined using Equation 5, and a speed of sound in brain tissue of 1570 meters per second (m/s). The propagation times for the rays R3, R4 may then be summed to yield a propagation time correcting for tissue inhomogeneity, including refraction, for the acoustic energy transmitted from the transducer element 16a.

Corrected propagation times for refracted rays transmitted from transducer element 16b and the other transducer elements 16 to the focal zone P1 may be computed in similar fashion. The corrected propagation times for each of the transducer elements 16 may be provided to a processor, such as the controller 20 coupled to the transducer 14 or the system image and display computer 40 (not shown, see FIG. 1), to determine corrective time delays for excitation signals delivered to each respective transducer element 16 such that the collective acoustic energy transmitted by the transducer 14 constructively interferes at the focal zone P1.

As mentioned above, if desired, refraction within multiple bone tissue layers, such as the three bone tissue layers 50, 52,

54 shown in FIG. 3, may also be considered when determining phase compensation due to distances traveled in the respective tissue layers as part of a three-layer model. For a three-layer model, it may be assumed that the skull consists of individual homogeneous layers, and that the speed of sound may correlate linearly to the bone density (and consequently to speed of sound), e.g., as measured by CT or ultrasound imaging. As an example, the speed of sound may be approximately 2500 meters per second (m/s) for the central layer 52 and approximately 2900 meters per second (m/s) for the inner and outer layers 50, 54. The expected phase shift across the skull 28 using this three-layer model is:

$$\phi = 360 f \sum_{n=1}^{3} D_n \left( \frac{1}{c_0} - \frac{1}{c_n} \right) \tag{7}$$

with $c_n$ equal to the speed of sound in the $n^{th}$ layer and $D_n$ being the thickness of the $n^{th}$ layer.

Because local density of the skull 28 may affect propagation through the skull 28, phase correction based on the skull's density may help improve focusing of ultrasound energy from the array 14. To assess the contribution of internal density variations to deviations from the expected single-layer homogeneous values (as calculated from Equation 3 above), the mean CT image intensity along the ultrasound axis of propagation (e.g., the vector 96 in FIG. 3) and the speed of sound may be correlated. Using a three-dimensional image, e.g., constructed from two-dimensional CT images, each voxel may be assigned an intensity value, assuming that the intensity is linearly proportional to bone density and the density is scaled to MKS units using air and water in the image as reference intensities. Mean intensity may be determined by summing the CT intensity values along the axis of propagation 96 inside the bone 28 and dividing by the total number summed of voxels. The voxels may include air-filled or liquid-filled pockets. The speed of sound for liquid-filled voxels is assumed to be the speed of sound in water. It is also assumed that complete reflection will occur when acoustic energy encounters an air-filled pocket.

Phase corrections due to skull density may be calculated empirically, e.g., as the difference between actual measured phase shift resulting from acoustic energy passing through the skull and the theoretical phase shift given by Equation 3 (for a single-layer model). An empirical correction factor has been obtained by fitting (using a polynomial curve fit) percent error as a function of the mean intensity, namely:

$$C(\rho) = \sum_{n=0}^{N} A_n \rho^{N-n} \tag{8}$$

where there are N+1 coefficients $A_n$ to be determined for an $N^{th}$ degree fit, and $\rho$ is the density. Applying a third order fit using a 117 point data set and five skulls at 0.51 Megahertz (MHz) yielded coefficients, in MKS units, of:

TABLE 1

| | |
|---|---|
| $A_0$ | 1.1424e−008 |
| $A_1$ | −7.5377e−005 |
| $A_2$ | 0.1645 |
| $A_3$ | −118.689 |

These coefficients may be used in Equation 8, and the resulting Equation 8 correction factor may be applied to Equation 3 as part of a single-layer homogeneous model to yield a corrected phase shift of:

$$\phi = \frac{\Phi}{1+C}, \tag{9}$$

where $\Phi$ contains the initial phase values obtained using Equation 3.

The density and thickness measurements may also be applied towards adjusting the skull speed of sound. To adjust the speed of sound value for a single layer, the speed may be fit as a function of density according to:

$$c_s(\rho) = \left[ \frac{1}{c_0} - \frac{\phi(\rho)}{360 f D} \right]^{-1} \tag{10}$$

where $\phi(\rho)$ is the measured phase shift as a function of density. A polynomial fit as shown in Equation 8 may be used to find the speed of sound values. For the three layer model, two speeds of sound are calculated. These two speeds are the speed $c_i$ for the cortical layers and the speed $c_{ii}$ of the trabecular (central) bone. Given the thicknesses $D_1$, $D_2$, and $D_3$, respectively, for the three bone layers 50, 52, 54, the speed $c_{ii}$ of the cortical layer is fit as a function of density according to:

$$c_i(\rho) = (D_1 + D_3) \left[ \frac{D_1 + D_2 + D_3}{c_0} - \frac{D_2}{c_{ii}} - \frac{\phi(\rho)}{360 f D} \right]^{-1}. \tag{11}$$

The polynomial fit for $c_i(\rho)$ is performed using Equation 8 over a series of trial functions for $c_{ii}$. The final speeds of sound are the $c_i(\rho)$ and $c_{ii}(\rho)$ that most closely correlate by standard deviation or other methods with direct skull measurements obtained by fitting a large sample of skulls.

The power supplied to a patient's skull depends on the type of therapy. During focused ultrasound ablation using a multiple element transducer array, approximately one to three electrical kilowatts (1-3 kW) may be delivered for approximately ten to thirty (10-30) seconds. To open the blood-brain barrier, about one hundred times less power than that used during ablation may be used, e.g., due to preformed gas bubbles in the area of interest. The ablation power may be reduced by the preformed gas bubbles. Using bursts of energy may also reduce, if not eliminate, effects on phase due to standing waves that may otherwise occur if the transducer elements 16 continuously transmit energy.

Figure 5:
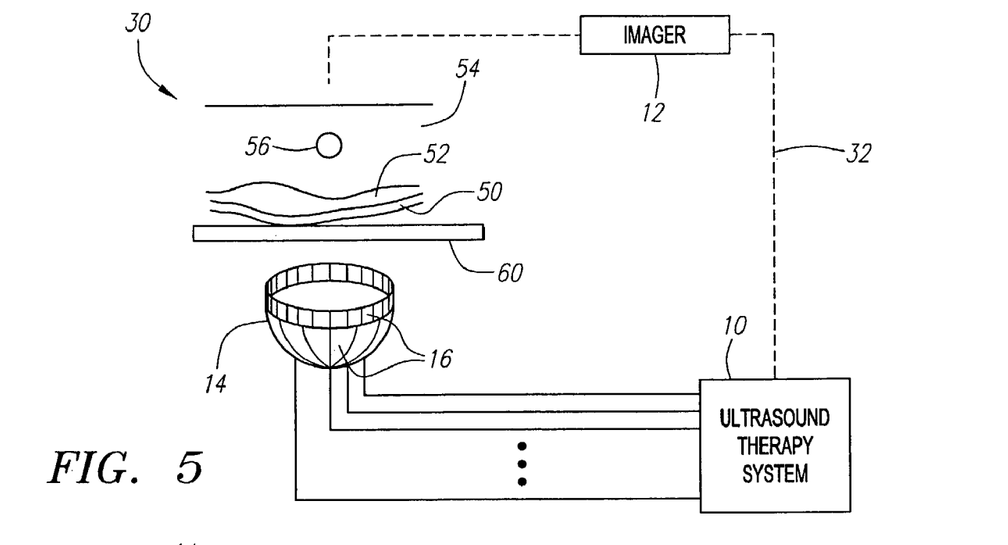
FIG. 5 is a cross sectional view of a portion of a patient's body being treated using the ultrasound therapy system of FIG. 1.

Turning to FIG. 5, the systems and methods described herein may also be used for transmitting acoustic energy to a target site within soft tissue, e.g., located behind a layer of fat. The ultrasound therapy system 10 may be identical or similar to the system 10 of FIG. 1, and so like reference numbers have been used for like components. A transducer 14 including a plurality of transducer elements 16 may be disposed on or near the exterior surface of the patient 30. The transducer 14 may assume any suitable shape including, for example, curved, planar, and/or parabolic shapes. Preferably, the transducer 14 is configured for focusing ultrasonic energy at a desired focal distance from the surface of the array 14, i.e., into the patient 30.

Where the pass zone includes soft tissue regions, such as one or more fat tissue regions, the phase shift of the acoustic energy may be corrected due to the fat tissue regions in the pass zone. Within soft tissue (i.e. not including bone tissue), fat tissue may create greater phase shifts than other soft tissue, such as muscles or organs. For example, the speed of sound in fat tissue is approximately 1460 meters per second (m/s), which is farther from the average speed of sound (approximately 1540 m/s) typically used in conventional procedures. As mentioned above, this difference in local speed of sound may cause a significant decrease in intensity of the acoustic energy delivered to the focal zone due to decreased constructive interference of the acoustic energy transmitted by collectively by the transducer elements.

Of other soft tissue types, muscle tissue has the next largest difference from the average speed of sound, namely sixteen hundred meters per second (approximately 1600 m/s). While muscle tissue may cause phase shifts that may decrease constructive interference, the impact is generally substantially less than that of fat tissue regions and therefore may be ignored in most cases. Among organ tissue, the speed of sound in livers is approximately 1555 meters per second (m/s), and the speed of sound in kidneys is approximately 1565 meters per second (m/s). Such small deviations from the average speed of sound may only cause small or negligible aberrations that may be ignored except where the highest transmission of ultrasound energy to the focal zone is required.

Since correcting for aberrations due to fat tissue regions provides the most improvement in energy transmission to the focal zone (compared to other soft tissues and assuming no bone tissue exists within the pass zone or phase corrections are provided for bone tissue within the pass zone), the fat tissue regions may be segmented and excitation correction factors computed based upon the actual speed of sound in, and refraction caused, by the fat tissue regions, similar to the methods described above for bone tissue.

Optionally, additional improvement in the correction, and hence additional improvement in energy transmission, may be obtained by segmenting muscle tissue regions and using the speed of sound in, and refraction caused by, the muscle tissue regions to calculate excitation correction factors. The remaining soft tissue regions (other than fat and muscle tissue regions) may be considered to be part of the muscle tissue regions, or may be separately segmented and analyzed, if desired.

Figure 6:
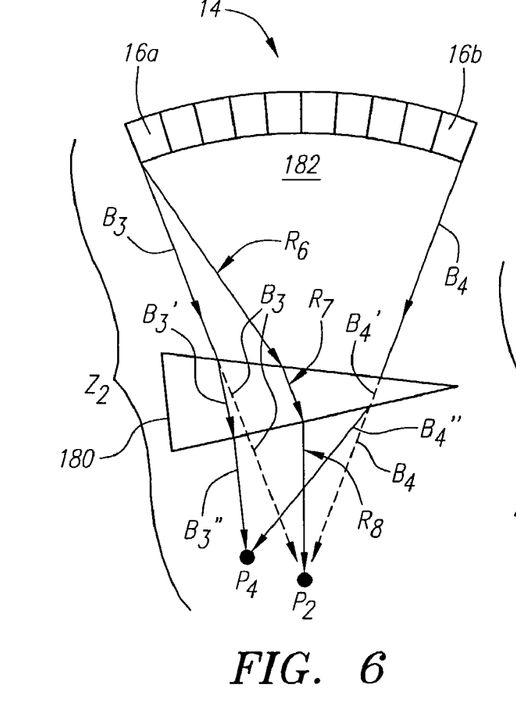
FIG. 6 is a schematic representation of beams of acoustic energy transmitted by a transducer array and refracted by a prism-shaped tissue region.

Depending upon the shape of segments of a tissue region, acoustic energy transmitted by a transducer may constructively interfere at an actual focal zone shifted in space with respect to the desired focal zone. For example, FIG. 6 shows an exemplary tissue region that includes a segmented fat tissue region 180 in a pass zone Z2 located between a transducer 14 and a desired focal zone P2. The remaining tissue 182 between the transducer 14 and the fat tissue region 180 is assumed to be muscle tissue. Other tissue regions in the pass zone Z2 are not shown to simplify the example. The exemplary segmented fat tissue region 180 has a uniformly changing thickness across a plane that extends substantially parallel to a plane defined by the transducer 14. The rate of change of depth with distance is monotonic (continuously increasing or decreasing) and linear (i.e., the boundary may be defined by the equation Y=a+bx). Such a tissue region may be modeled as a prism.

Two exemplary rays of acoustic energy B3, B4 are shown being transmitted from transducer elements 16a, 16b, respectively, on opposite ends of the transducer 14. The rays B3, B4 are intended to be focused on a desired focal zone P2, as demonstrated by dashed lines. The desired focal zone P2 may be selected by an operator for treatment, e.g., using an imaging system, as described above. As shown, however, refraction causes the two rays B3, B4 (and similarly acoustic energy transmitted by the other transducer elements 16 of the transducer 14), to be focused on a new focal zone P4 at a different location than the desired focal zone P2.

The actual paths of the beam B3, B4 through and after the prism of fat tissue 180 are indicated by solid lines B3', B3", B4', B4" (as compared with the dashed lines that indicate the path the acoustic energy would follow if there was no refraction). Since the rate of change of the depth of the tissue region 180 is monotonic and linear, the acoustic energy refracts proportionally across the acoustic beam as it passes through the tissue region 180. The phases of the beams are shifted proportionally in such a way that the beams are steered to constructively interfere at the actual focal zone P4. Constructive interference at the shifted focal zone P4 may not appreciably degraded, although the desired intensity of energy delivery may not occur at the desired focal zone P2.

The displacement of the focal zone P2 due to refraction by the tissue region 180 may be corrected, e.g., using the methodology described above with reference to FIG. 2, to steer the beam of acoustic energy back to the desired focal zone P2. Phase shift factors $\alpha_1$-$\alpha_n$ or corrected propagation times for each transducer element may be determined, e.g., using a forward or reverse ray calculation, as described above.

New rays R6, R7, R8 are shown as an actual path desired for acoustic energy transmitted by transducer element 16a taking into consideration Snell's law (Equation 4 above), the segmented boundaries of the tissue region 180, and the speeds of sound in the tissue region 180 and adjacent (muscle) tissue regions, similar to the methods described above. Similar rays, and resultant phase correction factors, may be computed for the other transducer elements 16 of the transducer 14 to provide a beam of acoustic energy that is focused on the focal zone P2.

While correction for focal zone shift is inherent in the correction process when refraction is considered, as described herein, software implementing the correction process may allow for separate corrections for defocusing (i.e., a decrease in constructive interference at the actual focal zone) and focal zone shift. In some circumstances, it may be desired or necessary to correct for only one or the other. For example, tissue aberration may redirect the focal zone to a location beyond which the electronic steering capabilities of the transducer can correct (e.g., because the elements are not small enough). In this case, a corrective algorithm may attempt to steer the focal zone back to the desired focal zone, but, because it cannot, most of the energy may not be delivered to the desired location. In this situation, the transducer may be moved mechanically, e.g., along the surface of the tissue structure, to relocate the focal zone towards the target site.

Figure 7:
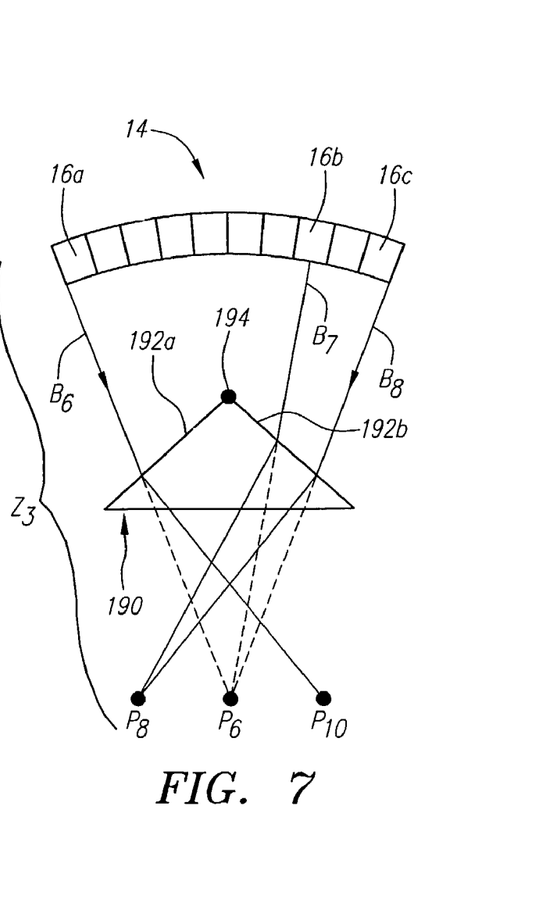
FIG. 7 is a schematic representation of beams of acoustic energy transmitted by a transducer array and refracted by a prism-shaped tissue region with a vertex facing the transducer array.

Turning to FIG. 7, another example of a segmented tissue region 190 is shown that may be modeled as a prism, where two faces 192a, 192b and a vertex 194 of the prism intercept the acoustic energy transmitted by the transducer 14. The rate of change of depth with distance through each face 192a, 192b is assumed to be monotonic and linear in this example for illustration. The tissue region 190 is located such that the acoustic energy transmitted by the transducer 14 is substantially bisected.

Three exemplary rays B6, B7, B8 of acoustic energy are shown being transmitted by respective transducer elements 16a, 16b, 16c. The acoustic energy represented by the rays B6, B7, B8 are intended to be focused onto a focal zone P6. Due to refraction by the prism shaped tissue region 190, however, the rays B7 and B8 (and other acoustic energy transmitted by transducer elements 16 that impinge upon the boundary 192b of the tissue region 190), are focused towards an actual focal zone P8. The ray B6 (and other acoustic energy transmitted by the transducer elements 16 that impinge upon the boundary 192a) are focused on a focal zone P10, thereby effectively bisecting the acoustic energy transmitted by the transducer 14.

The focal zones P8 and P10 may be symmetrically positioned with respect to the desired focal zone P6. Each shifted focal zones P8, P10 may receive about half of the acoustic energy intended for the desired focal zone P6. While the acoustic energy is divided and delivered to focal zones P8, P10 substantially symmetrically positioned with respect to the desired focal zone P6, the acoustic energy focused on each focal zone P8, P10 may constructively interfere within known tolerances. The beams of acoustic energy impinging upon each boundary of the tissue region 190 may be corrected, as described above, to focus the acoustic energy transmitted by the transducer 14 towards the desired focal zone P6.

Other embodiments are within the scope and spirit of the appended claims. For example, the transducer 14 shown in FIGS. 1 and 5 may include a different number of transducer elements 16 than that shown. The phase shift factors $\alpha_1$-$\alpha_n$ may be pre-stored in the channels of the signal adjuster 18 instead of being provided by the controller 20. Further, functions described above may be performed by the imager 12, the signal adjuster 18, the system image and display computer 40, and/or by an operator using the system 10, e.g., calculating densities, determining tissue types and/or tissue boundaries, and/or providing corrective data to the controller 20 and/or signal adjuster 18, e.g., phase shift factors $\alpha_1$-$\alpha_n$ and/or amplitudes of excitation signal used to drive the transducer elements 16.

Still further embodiments are within the scope and spirit of the appended claims. For example, while the above discussion focused on ultrasonic energy transmitted through human skulls and subcutaneous layers of fat, other frequencies of energy and other subjects may be used, and other regions within subjects may be targeted for treatment. For example, non-human subjects are acceptable, as well as transmitting energy into regions of human or non-human subjects aside from through the skull and layers of fat. Similar techniques may also be used to account for phase shifts introduced in omental (i.e., nonsubcutaneous) fat. Also, other techniques for determining and/or controlling the phase and amplitude of signals transmitted into a subject may be used. For example, techniques that may be used include those of U.S. patent application Ser. No. 09/724,817, filed Nov. 28, 2000, entitled "Systems and Methods for Focusing an-Acoustic Energy Beam Transmitted Through a Skull," and U.S. patent application Ser. No. 09/724,611, filed Nov. 28, 2000; entitled "Systems and Methods for Controlling a Phased Array Focused Ultrasound System." The disclosures of these references and any other references cited therein are expressly incorporated herein by reference.

Finally, while the present invention has been explained in the context of the preferred embodiments described above, it is to be understood that various changes may be made to those embodiments, and various equivalents may be substituted, without departing from the spirit or scope of the invention, as will be apparent to persons skilled in the relevant art.

What is claimed is:

1. A system for delivering acoustic energy through intervening tissue into a target site within a tissue region, comprising:
   a transducer array comprising a plurality of transducer elements configured for transmitting acoustic energy along respective pass zones through the intervening tissue towards the target site;
   an imager for imaging the tissue region, the imager generating image data indicating tissue types of the intervening tissue;
   a processor coupled to the imager for receiving the image data, the processor configured to determine boundaries between a plurality of tissue types within the intervening tissue and generate correction factors for the transducer elements to compensate for refraction occurring as the acoustic energy passes through the tissue types within the intervening tissue and for variations in speed of sound of the acoustic energy as it passes through the plurality of tissue types within the respective pass zones; and
   a controller coupled to the processor and the transducer array, the controller configured for receiving the correction factors from the processor and providing excitation signals to the transducer elements based upon the respective correction factors to focus the acoustic energy transmitted by the transducer elements at the target site.

2. The system of claim 1, wherein the imager comprises at least one of a magnetic resonance imager, a computer tomography imager, and an ultrasound imager.

3. The system of claim 1, wherein the imager is configured for generating intensity data comprising a relative density of respective tissue types, and wherein the processor is configured for analyzing the intensity data to identify the plurality of tissue types.

4. The system of claim 1, wherein the imager is configured for generating a plurality of two-dimensional images comprising the intervening tissue.

5. The system of claim 4, wherein the processor is configured for converting the plurality of two-dimensional images into one or more three-dimensional renderings comprising the intervening tissue.

6. The system of claim 5, wherein the processor is configured for automatically determining the boundaries between the plurality of tissue types within the intervening tissue based upon the one or more three-dimensional renderings.

7. The system of claim 5, further comprising:
   a display configured to display the one or more three-dimensional renderings; and
   a user interface configured to interact with the one or more three-dimensional renderings to identify tissue types within the intervening tissue.

8. The system of claim 4, wherein the processor is configured for automatically determining the boundaries between the plurality of tissue types based upon the two-dimensional images.

9. The system of claim 1, wherein the correction factors comprise phase correction factors associated with respective transducer elements, and wherein the controller comprises a phase adjuster configured to adjust phases of excitation signals provided to the respective transducer elements based upon the phase correction factors.

10. The system of claim 9, wherein the excitation factors comprise amplitude correction factors associated with respective transducer elements, and wherein the controller further comprises one or more amplifiers coupled to the phase adjuster configured to amplify the excitation signals provided to the respective transducer elements based upon the amplitude correction factors.

11. A method for focusing acoustic energy transmitted from a plurality of transducer elements of a transducer array through intervening tissue at a target site within a tissue region, the method comprising:
   acquiring one or more images of a portion of the tissue region that includes the intervening tissue and the target site;
   determining boundaries between a plurality of tissue types within the intervening tissue from the one or more images;
   generating respective excitation correction factors for each transducer element of the transducer array to compensate for refraction occurring as the acoustic energy passes through the tissue types within the intervening tissue and to compensate for variations in speed of sound of the acoustic energy as it passes through the plurality of tissue types within pass zones extending from respective transducer elements through the intervening tissue to the target site; and
   administering acoustic energy from the transducers to the target site in response to the excitation factors.

12. The method of claim 11, further comprising driving the transducer elements with respective excitation signals based upon the respective excitation correction factors, thereby focusing acoustic energy from the transducer array at the target site.

13. The method of claim 12, wherein sufficient acoustic energy is focused at the target site for sufficient time to ablate tissue at the target site.

14. The method of claim 11, wherein the excitation correction factors comprise phase shift factors, and wherein the step of generating respective excitation correction factors comprises generating the phase shift factors, at least in part, by conducting ray calculations between the target site and each transducer element.

15. The method of claim 11, wherein the excitation correction factors comprise time delays, and wherein the step of generating respective excitation correction factors comprises determining a respective propagation time along a pass zone extending from each transducer element through boundaries between successive tissue types within the intervening tissue to the target site, the propagation time based, at least in part, upon the speed of sound in the successive tissue types, refraction at the boundaries between the successive tissue types, and a distance of the pass zone between the respective transducer element and the target site.

16. The method of claim 11, wherein the respective excitation correction factors are generated to correct for at least one of displacement of a focal zone of the transducer away from the target site and defocusing of a focal zone of the transducer array at the target site.

17. The method of claim 11, wherein the target site comprises a tissue structure within a brain, and the intervening tissue comprises bone tissue.

18. The method of claim 11, wherein the intervening tissue further comprises fat tissue.

19. The method of claim 11, wherein the one or more images comprise a plurality of image slices selected from magnetic resonance images, computer tomography images, or ultrasound images of the tissue region comprising the target site and the intervening tissue.

20. The method of claim 19, wherein the step of determining the boundaries comprises:
   volumetrically reconstructing a three-dimension rendering of the tissue region from the image slices;
   identifying regions of different tissue types within the tissue region based upon the three-dimensional rendering; and
   determining three-dimensional boundaries between the identified regions of different tissue types within the tissue region.

21. A method for focusing acoustic energy to ablate a target site within a tissue region using a transducer array comprising a plurality of transducer elements, the method comprising:
   acquiring one or more images of a portion of the tissue region that includes the target site and intervening tissue between the transducer array and the target site;
   determining boundaries between a plurality of tissue types within the intervening tissue based upon the one or more images;
   generating respective correction factors for each transducer element of the transducer array to compensate for refraction occurring as the acoustic energy passes through the tissue types within pass zones extending from respective transducer elements through the intervening tissue to the target site and for variations in speed of sound of the acoustic energy as it passes through the plurality of tissue types within the pass zones; and
   driving the transducer elements with excitation signals based upon the correction factors to focus acoustic energy from the transducer elements at the target site for sufficient time to ablate tissue at the target site.

22. The method of claim 21, wherein the acquired images comprise a plurality of two-dimensional images comprising the intervening tissue.

23. The method of claim 22, wherein the step of determining boundaries comprises:
   converting the plurality of two-dimensional images into a three-dimensional rendering comprising the intervening tissue; and
   determining the boundaries between the plurality of tissue types within the intervening tissue based upon the three-dimensional rendering.

24. The method of claim 21, wherein the correction factors comprise phase correction factors associated with respective transducer elements, and wherein the phases of excitation signals provided to the respective transducer elements are adjusted based upon the phase correction factors.

25. The method of claim 24, wherein the excitation factors comprise amplitude correction factors associated with respective transducer elements, and wherein the excitation signals provided to the respective transducer elements are amplified based upon the amplitude correction factors.

26. Software to operate an ultrasound therapy system including a transducer array including a plurality of transducer elements, the software residing on a computer readable medium and comprising instructions to cause the system to:
   acquire one or more images of a tissue region comprising a target site and intervening tissue between the transducer array and the target site;
   determine boundaries between a plurality of tissue types within the intervening tissue based upon the one or more images; and
   generate excitation correction factors for the transducer elements to compensate for variations in speed of sound of the acoustic energy as it passes through the plurality of tissue types within pass zones extending from respective transducer elements through the intervening tissue to the target site and to compensate for refraction occurring as the acoustic energy passes through the boundaries between the tissue types within the pass zones.

* * * * *